United States Patent
Popple et al.

(10) Patent No.: US 10,073,438 B2
(45) Date of Patent: Sep. 11, 2018

(54) ASSESSING MACHINE TRAJECTORIES FOR COLLISION AVOIDANCE

(71) Applicant: THE UAB RESEARCH FOUNDATION, Birmingham, AL (US)

(72) Inventors: Richard Popple, Homewood, AL (US); Rex Cardan, Hoover, AL (US)

(73) Assignee: The UAB Research Foundation, Birmingham, AL (US)

( * ) Notice: Subject to any disclaimer, the term of this patent is extended or adjusted under 35 U.S.C. 154(b) by 282 days.

(21) Appl. No.: 14/908,763

(22) PCT Filed: Jul. 31, 2014

(86) PCT No.: PCT/US2014/049097
§ 371 (c)(1),
(2) Date: Jan. 29, 2016

(87) PCT Pub. No.: WO2015/017639
PCT Pub. Date: Feb. 5, 2015

(65) Prior Publication Data
US 2016/0161938 A1    Jun. 9, 2016

Related U.S. Application Data

(60) Provisional application No. 61/860,542, filed on Jul. 31, 2013.

(51) Int. Cl.
*G05B 19/40* (2006.01)
*G05B 19/4061* (2006.01)
*A61N 5/10* (2006.01)

(52) U.S. Cl.
CPC .......... *G05B 19/4061* (2013.01); *A61N 5/103* (2013.01); *A61N 5/1049* (2013.01);
(Continued)

(58) Field of Classification Search
CPC ...... G05B 19/4061; G05B 2219/49137; G05B 2219/45169; A61N 5/1049; A61N 5/103
See application file for complete search history.

(56) References Cited

U.S. PATENT DOCUMENTS

| 7,835,494 B2* | 11/2010 | Nord ............... A61N 5/1031 378/65 |
| 2013/0060146 A1 | 3/2013 | Yang et al. |
| 2013/0142310 A1 | 6/2013 | Fahimian et al. |

FOREIGN PATENT DOCUMENTS

WO    2011073599 A1    6/2011

OTHER PUBLICATIONS

Supplementary European Search Report for EP 14 83 1436 dated May 23, 2017.
(Continued)

*Primary Examiner* — Vanthu Nguyen
(74) *Attorney, Agent, or Firm* — Thomas Horstemeyer, LLP (57) ABSTRACT

Disclosed are various embodiments for assessing machine trajectories for collision avoidance. A three-dimensional model of a patient based at least in part on data received from a three-dimensional imaging device is generated. The three-dimensional model of the patient is aligned with a coordinate system of a three-dimensional model of a radiation treatment machine. It is then determined whether a collision between the patient and the radiation treatment machine will occur at each one of a series of control points of the radiation treatment plan.

15 Claims, 4 Drawing Sheets

(52) U.S. Cl.
CPC .............. *G05B 2219/45169* (2013.01); *G05B 2219/49137* (2013.01)

(56) References Cited

OTHER PUBLICATIONS

International Search Report for PCT/US2014/049097 dated Nov. 20, 2014.
Yang Y, Zhang P, Happersett L, et al. Choreographing Couch and Collimator in Volumetric Modulated Arc Therapy. Int J Radiat Oncol Biol Phys 2011.
Besl P, McKay N. A Method for Registration of 3-D Shapes. IEEE Trans Pattern Anal Machine Intel 1992:239-256.
Humm JL, Pizzuto D, Fleischman E, et al. Collision detection and avoidance during treatment planning. Int J Radiat Oncol Biol Phys 1995;33:1101-1108.
Ward JW, Phillips R, Williams T, et al. Immersive visualization with automated collision detection for radiotherapy treatment planning. Stud Health Technol Inform 2007;125:491-496.
Tsiakalos MF, Scherebmann E, Theodorou K, et al. Graphical treatment simulation and automated collision detection for conformal and stereotactic radiotherapy treatment planning. Med Phys 2001;28:1359-1363.
Nioutsikou E, Bedford JL, Webb S. Patient-specific planning for prevention of mechanical collisions during radiotherapy. Phys Med Biol 2003;48:N313-321.
Hamza-Lup FG, Sopin I, Zeidan O. Comprehensive 3D visual simulation for radiation therapy planning. Stud Health Technol Inform 2007;125:164-166.
Humm JL. Collision avoidance in computer optimized treatment planning. Med Phys 1994;21:1053-1064.
Kessler ML, McShan DL, Fraass BA. A computer-controlled conformal radiotherapy system. III: Graphical simulation and monitoring of treatment delivery. Int J Radiat Oncol Biol Phys 1995;33:1173-1180.
Chao MM, Chao LS, Chen YJ, et al. Image display for collision avoidance of radiation therapy: treatment planning. J Digit Imaging 2001;14:186-191.
Yan Y, Song Y, Boyer AL. An investigation of a video-based patient repositioning technique. Int J Radiat Oncol Biol Phys 2002;54:606-614.
Bert C, Metheany KG, Doppke K, et al. A phantom evaluation of a stereo-vision surface imaging system for radiotherapy patient setup. Med Phys 2005;32:2753-2762.
Djajaputra D, Li S. Real-time 3D surface-image-guided beam setup in radiotherapy of breast cancer. Med Phys 2005;32:65-75.
Meeks SL, Tome WA, Willoughby TR, et al. Optically guided patient positioning techniques. Semin Radiat Oncol 2005;15:192-201.
Schoffel PJ, Harms W, Sroka-Perez G, et al. Accuracy of a commercial optical 3D surface imaging system for realignment of patients for radiotherapy of the thorax. Phys Med Biol 2007;52:3949-3963.
Brahme A, Nyman P, Skatt B. 4D laser camera for accurate patient positioning, collision avoidance, image fusion and adaptive approaches during diagnostic and therapeutic procedures. Med Phys 2008;35:1670-1681.
Moser T, Fleischhacker S, Schubert K, et al. Technical performance of a commercial laser surface scanning system for patient setup correction in radiotherapy. Phys Med 2010.

\* cited by examiner

ASSESSING MACHINE TRAJECTORIES FOR COLLISION AVOIDANCE

CROSSREFERENCE TO RELATED APPLICATIONS

This application is the 35 U.S.C. § 371 national stage application of PCT Application No. PCT/US2014/049097, filed Jul. 31, 2014, which claims priority to U.S. Provisional Application 61/860,542, filed on Jul. 31, 2013, both of which are incorporated by reference herein in their entirety.

BACKGROUND

During radiation therapy, there is potential for the treatment machine, such as a linear accelerator, to collide with either the patient, the patient support system, such as the treatment table, or other equipment. Such collisions can result in patient injury and/or death as well as equipment damage. To avoid collisions, the treatment geometry is inspected by a therapist before initiation of treatment. If a potential collision geometry is found, the treatment is terminated and a revised treatment plan is created. This process requires several days and is inconvenient for the patient and costly for the provider. To avoid such situation, planners use intuition and are very conservative in the choice of treatment geometry. This inhibits the use of more advanced treatment techniques in which the machine and patient move during treatment. These advanced techniques require computer-assisted collision prediction in advance of treatment, because the advanced treatment techniques use geometries too complex for human planners to visualize.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

SUMMARY

Disclosed are various embodiments for a system comprising one or more circuits, one or more processors, or any combination thereof, configured to at least: generate a three-dimensional model of a patient; identify a series of control points corresponding to movement of at least one of three-dimensional model of the patient or a three-dimensional model of a treatment machine; and determine whether the three-dimensional model of the patient and the three-dimensional model of the treatment machine overlap at each one of the series of control points. In some embodiments, the one or more circuits, one or more processors, or any combination thereof, are further configured to identify a collision between the patient and the treatment machine based at least in part on a determination that the three-dimensional model of the patient and the three-dimensional model of the treatment machine overlap at at least one of the series of control points. In some embodiments, the three-dimensional model of the patient is based at least in part on a point map provided by a three-dimensional imaging device in data communication with the one or more circuits, one or more processors, or any combination thereof. In some embodiments, the one or more circuits, one or more processors, or any combination thereof, are further configured to at least: interpolate an additional point based at least in part on at least two control points in the series of control points; and determine whether the three-dimensional model of the patient and the three-dimensional model of the treatment machine overlap at the interpolated additional point. In some embodiments, the one or more circuits, one or more processors, or any combination thereof, are further configured to at least: interpolate an additional point based at least in part on at least two control points in the series of control points; and determine whether the three-dimensional model of the patient and the three-dimensional model of the treatment machine overlap at the interpolated additional point.

Disclosed are various embodiments for a system, comprising: a data store comprising: a three-dimensional model of a radiation treatment machine, and a radiation treatment plan comprising a series of control points; a computing device; a three-dimensional imaging device in network communication with the computing device; and an application executed in the computing device, the application comprising: logic that generates a three-dimensional model of a patient based at least in part on data received from the three-dimensional imaging device; logic that aligns the three-dimensional model of the patient with a coordinate system of the three-dimensional model of the radiation treatment machine; and logic that determines whether a collision between the patient and the radiation treatment machine will occur at each one of the series of control points of the radiation treatment plan. In some embodiments, the data received from the three-dimensional imaging device comprises a point cloud. In some embodiments, the application further comprises: logic that interpolates a position between two control points in the series of control points; and logic that determines whether a collision between the patient and the radiation treatment machine will occur at the interpolated position between the two control points. In some embodiments, the radiation treatment plan is a first radiation treatment plan, the series of control points is a first series of control points, and the application further comprises: logic that determines whether a collision between the patient and the radiation treatment machine will occur at each one of a second series of control points of a second radiation treatment plan in response to a determination that the collision between the patient and the radiation treatment machine will occur at at least one of the first series of control points of the first radiation treatment plan. In some embodiments, the three-dimensional imaging device comprises a hand-held three-dimensional scanner.

Disclosed are various embodiments for a computer-implemented method, comprising: generating, via a computing device, a three-dimensional model of a patient based at least in part on data received from a three-dimensional imaging device in network communication with the computing device; aligning, via the computing device, the three-dimensional model of the patient with a coordinate system of a three-dimensional model of a radiation treatment machine; and determining, via the computing device, whether a collision between the patient and the radiation treatment machine will occur at each one of a series of control points of a radiation treatment plan. In some embodiments, the method further comprises approving, via the computing device, the radiation treatment plan in response to a determination by the computing device that the collision between the patient and the radiation treatment machine will not occur. In some embodiments, the method further comprises: rejecting, via the computing device, the radiation treatment plan in response to a determination by the computing device that the collision between the patient and the radiation treatment machine will occur at at least one of the series of control points of the radiation treatment plan. In some embodiments, the three-dimensional model of the patient comprises a mesh wire-frame and the data from the three-dimensional imaging device comprises a point cloud. In some embodiments, determining whether a collision between the patient and the radiation treatment machine will occur comprises: identifying, via the computing device, a bounded space occupied by the three-dimensional model of the patient at each one of the series of control points of the radiation treatment plan; identifying, via the computing device, a bounded space occupied by the three-dimensional model of the radiation treatment machine; and determining, via the computing device, whether the bounded space occupied by the three-dimensional model of the patient overlaps, at least in part, the bounded space occupied by the three-dimensional model of the radiation treatment machine at each one of the series of control points of the radiation treatment plan.

DETAILED DESCRIPTION

Various embodiments are disclosed for predicting collisions during the treatment planning process. Three-dimensional (3-D) images of the patient and patient support systems, such as the treatment table, are obtained, for example using an optical camera. A 3-D model of the patient, patient support systems, and the treatment machine is used to identify configurations of the patient, patient support systems, and treatment machine that would result in a collision. In the following discussion, a general description of the system and its components is provided, followed by a discussion of the operation of the same.

Figure 1:
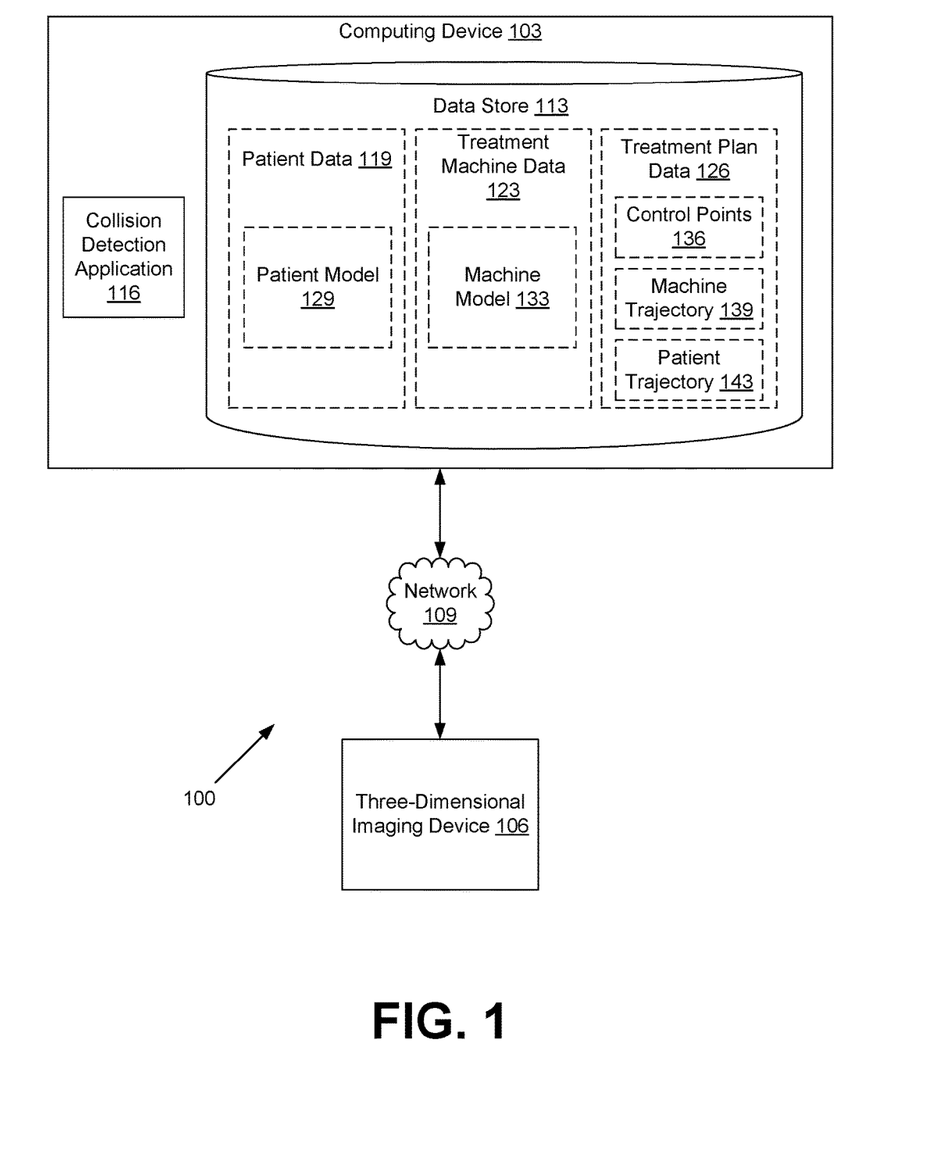
FIG. 1 is a drawing of a networked environment according to various embodiments of the present disclosure.

With reference to FIG. 1, shown is a networked environment 100 according to various embodiments. The networked environment 100 includes a computing device 103, and a three-dimensional imaging device 106, which are in data communication with each other via a network 109. The network 109 includes, for example, the Internet, intranets, extranets, wide area networks (WANs), local area networks (LANs), wired networks, wireless networks, direct connections, or other suitable networks, etc., or any combination of two or more such networks. For example, such networks can comprise satellite networks, cable networks, Ethernet networks, and other types of networks.

The computing device 103 can comprise, for example, a server computer or any other system providing computing capability. Alternatively, the computing device 103 can be one of a plurality of computing devices that can be arranged, for example, in one or more server banks or computer banks or other arrangements. Such computing devices can be located in a single installation or can be distributed among many different geographical locations. For example, the computing device 103 can be one of a plurality of computing devices that together can comprise a hosted computing resource, a grid computing resource and/or any other distributed computing arrangement. In some cases, the computing device 103 can correspond to an elastic computing resource where the allotted capacity of processing, network, storage, or other computing-related resources can vary over time.

Various applications and/or other functionality can be executed in the computing device 103 according to various embodiments. Also, various data is stored in a data store 113 that is accessible to the computing device 103. The data store 113 can be representative of a plurality of data stores 113 as can be appreciated. The data stored in the data store 113, for example, is associated with the operation of the various applications and/or functional entities described below.

The components executed on the computing device 103, for example, include the collision detection application 116, and other applications, services, processes, systems, engines, or functionality not discussed in detail herein. The collision detection application 116 is executed to identify collisions between patients and therapy machines, such as radiation therapy machines.

The data stored in the data store 113 includes, for example, patient data 119, treatment machine data 123, treatment plan data 126, and potentially other data.

The patient data 119 can represent personal data and the medical history of a patient, as well as other data. Include in the patient data 119 can be one or more three-dimensional patient models 129 of a patient. The three-dimensional patient model 129 can be generated from a point cloud or other data provided by the three-dimensional imaging device 106, as will be further discussed herein. In some embodiments, the three-dimensional patient model 129 can include a model of the patient as well as any supporting or immobilizing devices connected to the patient, such as a treatment, bed, table, and/or other device. It is understood that these supporting or immobilizing can be moved, in some embodiments, in order to move the patient in relation to a treatment machine.

The treatment machine data 123 can represent the make, model, manufacturer, capabilities, optimal parameters, and other data of a treatment machine, such as a radiation treatment machine. Also include in the treatment machine data 123 can be a three-dimensional treatment machine model 133. The three-dimensional treatment machine model 133 can be representative of a computer-assisted design (CAD) model provided by the manufacturer of the corresponding treatment machine, or can represent a three-dimensional model previously created, for example by using the three-dimensional imaging device 106. In some embodiments, the treatment machine data 123 may also include accessories for the treatment machine, such as intravenous (IV) poles and lines, ventilators, and/or other devices.

The treatment plan data 126 can represent data particular to a proposed treatment of a patient using a treatment machine. The treatment plan data 126 can include a series of control points 136, which are points in space and/or time in which a machine trajectory 139 and/or a patient trajectory 143 are analyzed to determine if collision between the patient and the treatment machine during treatment will occur. The machine trajectory 139 represents the path made by one or more components of the treatment machine and/or the path made by the treatment machine itself during the course of treatment. The patient trajectory 143 represents the path made by the patient during the course of treatment. For example, an oncology patient can be rotated and repositioned during the course of a radiation treatment for his or her cancer in conjunction with movements made by a radiation treatment machine or components of the radiation treatment machine in order to optimize the treatment of the patient.

The three-dimensional imaging device 106 is representative of a plurality of client devices that can be coupled to the network 109. In some embodiments, the three-dimensional imaging device 106 can comprise a three-dimensional scanner, a depth imaging camera, or similar device. In other embodiments, The three-dimensional imaging device 106 can comprise, for example, a processor-based system such as a computer system. Such a computer system can be embodied in the form of a desktop computer, a laptop computer, personal digital assistants, cellular telephones, smartphones, web pads, tablet computer systems, or other devices with like capability. In such embodiments, a three-dimensional camera can be attached to the processor-based system to provide the ability to for the processor-based system to generate three-dimensional images. The three-dimensional imaging device 106 can include a display. The display can comprise, for example, one or more devices such as liquid crystal display (LCD) displays, gas plasma-based flat panel displays, organic light emitting diode (OLED) displays, electrophoretic ink (E ink) displays, LCD projectors, or other types of display devices, etc.

Next, a general description of the operation of the various components of the networked environment 100 is provided. To begin, a patient and a treatment machine are placed in position for treatment. The three-dimensional imaging device 106 then scans the patient, for example using a three-dimensional scanner, an infrared depth camera, or similar device. The three-dimensional imaging device 106 sends the data related to the scan of the patient across the network 109 to the computing device 103. The collision detection application 116 then generates a three-dimensional patient model 129 using the data received from the three-dimensional imaging device 106. Subsequently, the collision detection application 116 aligns the three-dimensional patient model 129 with the coordinate system used by three-dimensional machine model 133 of the treatment machine. The collision detection application 116 then calculates whether the three-dimensional patient model 129 and the three-dimensional machine model 133 overlap at one or more control points 136 of a treatment plan 126. In some embodiments, the collision detection application 116 can use the machine trajectory 139 and the patient trajectory 143 to interpolate additional points between two or more control points for predicting collisions between a patient and a treatment machine. If a collision between the patient and the treatment machine is predicted by the collision detection application 116, then the treatment plan can be rejected by the collision detection application 116. If no collision is predicted by the collision detection application 116, then the treatment plan can be validated or otherwise approved by the collision detection application 116.

Figure 2:
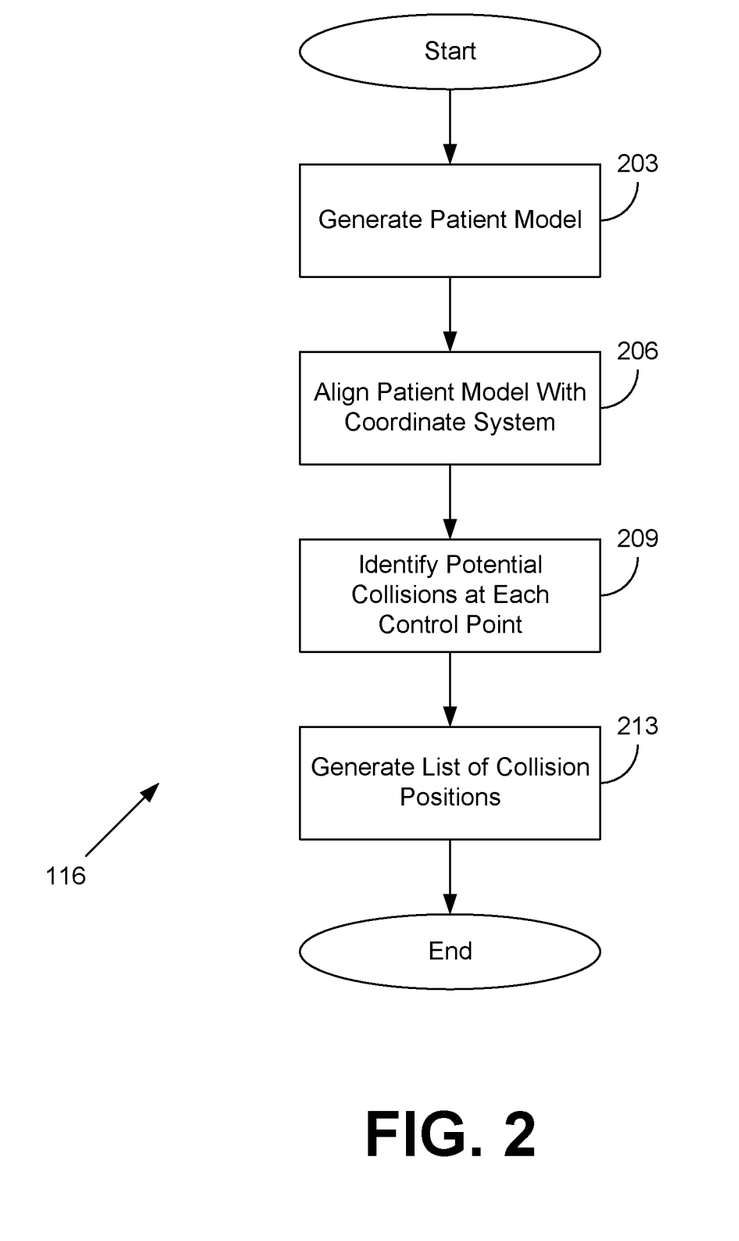
FIG. 2 is a flowchart illustrating one example of functionality implemented as portions of a collision detection application executed in a computing device in the networked environment of FIG. 1 according to various embodiments of the present disclosure.

Referring next to FIG. 2, shown is a flowchart that provides one example of the operation of a portion of the collision detection application 116 according to various embodiments. It is understood that the flowchart of FIG. 2 provides merely an example of the many different types of functional arrangements that can be employed to implement the operation of the portion of the collision detection application 116 as described herein. As an alternative, the flowchart of FIG. 2 can be viewed as depicting an example of elements of a method implemented in the computing device 103 (FIG. 1) according to one or more embodiments.

Beginning with box 203, the collision detection application 116 generates a three-dimensional patient model 129 (FIG. 1) based at least in part on data received from the three-dimensional imaging device 106 (FIG. 1). For example, the collision detection application 116 can generate a wire-frame model and/or a mesh model based at least in part on a point cloud provided by the three-dimensional imaging device 106. The point cloud can be obtained by the three-dimensional imaging device 106 using optical scanning methods or using infrared depth mapping.

Proceeding next to box 206, the collision detection application 116 aligns the three-dimensional patient model 129 with the coordinate system of the radiation treatment machine model 133.

Moving on to box 209, the collision detection application 116 determines whether a collision will occur at each one of a series of control points 136 (FIG. 1) related to treatment plan 126 (FIG. 1). At each of the control points 136, the collision detection application 116 can identify whether the three-dimensional patient model 129 overlaps the radiation treatment machine model 133. If an overlap is detected, this can indicate a potential collision. In some embodiments, the collision detection application 116 can interpolate additional points, based at least in part on the control points 136, the patient trajectory 139 (FIG. 1), and/or the machine trajectory 143 (FIG. 1). In such embodiments, the collision detection application 116 can identify whether the three-dimensional patient model 129 overlaps the radiation treatment machine model 133 at the interpolated points in a similar manner.

Referring next to box 213, the collision detection application 116 generates a list of collision positions that were determined in box 209. Execution subsequently ends.

Figure 3:
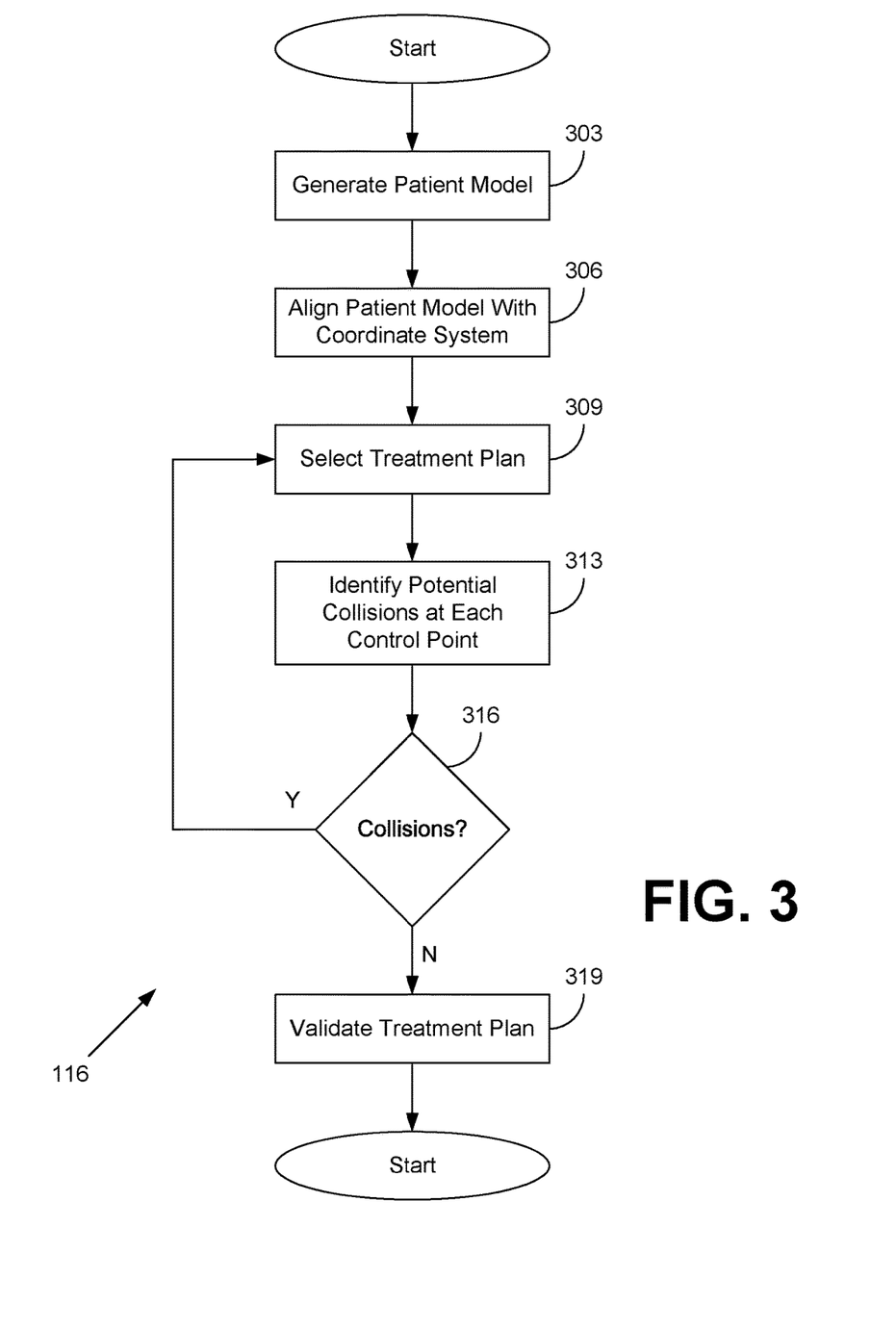
FIG. 3 is a flowchart illustrating one example of functionality implemented as portions of a collision detection application executed in a computing device in the networked environment of FIG. 1 according to various embodiments of the present disclosure.

Referring next to FIG. 3, shown is a flowchart that provides one example of the operation of a portion of the collision detection application 116 according to various embodiments. It is understood that the flowchart of FIG. 3 provides merely an example of the many different types of functional arrangements that can be employed to implement the operation of the portion of the collision detection application 116 as described herein. As an alternative, the flowchart of FIG. 3 can be viewed as depicting an example of elements of a method implemented in the computing device 103 (FIG. 1) according to one or more embodiments.

Beginning with box 303, the collision detection application 116 generates a three-dimensional patient model 129 (FIG. 1) based at least in part on data received from the three-dimensional imaging device 106 (FIG. 1). For example, the collision detection application 116 can generate a wire-frame model and/or a mesh model based at least in part on a point cloud provided by the three-dimensional imaging device 106. The point cloud can be obtained by the three-dimensional imaging device 106 using optical scanning methods or using infrared depth mapping.

Proceeding next to box 306, the collision detection application 116 aligns the three-dimensional patient model 129 with the coordinate system of the radiation treatment machine model 133. Moving on to box 309, the collision detection application 116 selects a treatment plan 126 (FIG. 1) for analysis.

Referring next to box 313, the collision detection application 116 determines whether a collision will occur at each one of a series of control points 136 (FIG. 1) related to the selected treatment plan 126. At each of the control points 136, the collision detection application 116 can identify whether the three-dimensional patient model 129 overlaps the radiation treatment machine model 133. If an overlap is detected, this can indicate a potential collision. In some embodiments, the collision detection application 116 can interpolate additional points, based at least in part on the control points 136, the patient trajectory 139 (FIG. 1), and/or the machine trajectory 143 (FIG. 1). In such embodiments, the collision detection application 116 can identify whether the three-dimensional patient model 129 overlaps the radiation treatment machine model 133 at the interpolated points in a similar manner.

Proceeding next to box 316, the collision detection application 116 determines whether any potential collisions were detected during the operations of box 313. If potential collisions were detected, the collision detection application 116 marks the treatment plan 126 as invalid and execution loops back to box 309. If no potential collisions were detected, then execution proceeds on box 319.

Moving on to box 319, the collision detection application 116 validates the treatment plan 126. Validation can include, for example, sending a copy of the treatment plan 126 to a client device, or causing a message to be rendered on a display of the computing device 103 (FIG. 1) indicating that the treatment plan 126 does not appear to contain any collisions. Execution subsequently ends.

Figure 4:
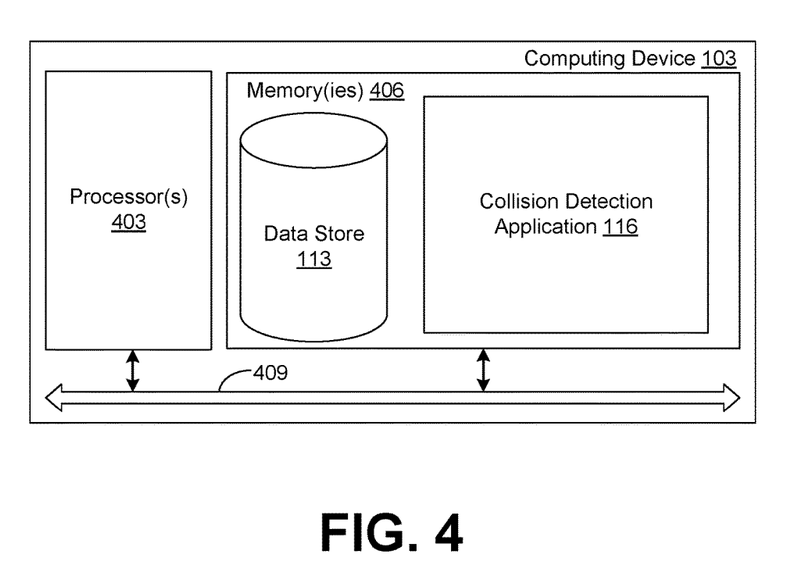
FIG. 4 is a schematic block diagram that provides one example illustration of a computing device employed in the networked environment of FIG. 1 according to various embodiments of the present disclosure.

With reference to FIG. 4, shown is a schematic block diagram of the computing device 103 according to an embodiment of the present disclosure. The computing device 103 includes at least one processor circuit, for example, having a processor 403 and a memory 406, both of which are coupled to a local interface 409. To this end, the computing device 103 can comprise, for example, a server computer or like device. The local interface 409 can comprise, for example, a data bus with an accompanying address/control bus or other bus structure as can be appreciated.

Stored in the memory 406 are both data and several components that are executable by the processor 403. In particular, stored in the memory 406 and executable by the processor 403 are list of main applications, and potentially other applications. Also stored in the memory 406 can be a data store 1113 and other data. In addition, an operating system can be stored in the memory 406 and executable by the processor 403.

It is understood that there can be other applications that are stored in the memory 406 and are executable by the processor 403 as can be appreciated. Where any component discussed herein is implemented in the form of software, any one of a number of programming languages can be employed such as, for example, C, C++, C#, Objective C, Java®, JavaScript®, Perl, PHP, Visual Basic®, Python®, Ruby, Flash®, or other programming languages.

A number of software components are stored in the memory 406 and are executable by the processor 403. In this respect, the term "executable" means a program file that is in a form that can ultimately be run by the processor 403. Examples of executable programs can be, for example, a compiled program that can be translated into machine code in a format that can be loaded into a random access portion of the memory 406 and run by the processor 403, source code that can be expressed in proper format such as object code that is capable of being loaded into a random access portion of the memory 406 and executed by the processor 403, or source code that can be interpreted by another executable program to generate instructions in a random access portion of the memory 406 to be executed by the processor 403, etc. An executable program can be stored in any portion or component of the memory 406 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 406 is defined herein as including both volatile and nonvolatile memory and data storage components. Volatile components are those that do not retain data values upon loss of power. Nonvolatile components are those that retain data upon a loss of power. Thus, the memory 406 can comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM can comprise, for example, static random access memory (SRAM), dynamic random access memory (DRAM), or magnetic random access memory (MRAM) and other such devices. The ROM can comprise, for example, a programmable read-only memory (PROM), an erasable programmable read-only memory (EPROM), an electrically erasable programmable read-only memory (EEPROM), or other like memory device.

Also, the processor 403 can represent multiple processors 403 and/or multiple processor cores and the memory 406 can represent multiple memories 406 that operate in parallel processing circuits, respectively. In such a case, the local interface 409 can be an appropriate network that facilitates communication between any two of the multiple processors 403, between any processor 403 and any of the memories 406, or between any two of the memories 406, etc. The local interface 409 can comprise additional systems designed to coordinate this communication, including, for example, performing load balancing. The processor 403 can be of electrical or of some other available construction.

Although the collision detection application 116, and other various systems described herein, can be embodied in software or code executed by general purpose hardware as discussed above, as an alternative the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowcharts of FIGS. 2 and 3 show the functionality and operation of an implementation of portions of the collision detection application 116. If embodied in software, each block can represent a module, segment, or portion of code that comprises program instructions to implement the specified logical function(s). The program instructions can be embodied in the form of source code that comprises human-readable statements written in a programming language or machine code that comprises numerical instructions recognizable by a suitable execution system such as a processor 403 in a computer system or other system. The machine code can be converted from the source code, etc. If embodied in hardware, each block can represent a circuit or a number of interconnected circuits to implement the specified logical function(s).

Although the flowcharts of FIGS. 2 and 3 show a specific order of execution, it is understood that the order of execution can differ from that which is depicted. For example, the order of execution of two or more blocks can be scrambled relative to the order shown. Also, two or more blocks shown in succession in FIGS. 2 and 3 can be executed concurrently or with partial concurrence. Further, in some embodiments, one or more of the blocks shown in FIGS. 2 and 3 can be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the collision detection application 116, that comprises software or code can be embodied in any non-transitory computer-readable medium for use by or in connection with an instruction execution system such as, for example, a processor 403 in a computer system or other system. In this sense, the logic can comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium can be a random access memory (RAM) including, for example, static random access memory (SRAM) and dynamic random access memory (DRAM), or magnetic random access memory (MRAM). In addition, the computer-readable medium can be a read-only memory (ROM), a programmable read-only memory (PROM), an erasable programmable read-only memory (EPROM), an electrically erasable programmable read-only memory (EEPROM), or other type of memory device.

Further, any logic or application described herein, including list of main applications, can be implemented and structured in a variety of ways. For example, one or more applications described can be implemented as modules or components of a single application. Further, one or more applications described herein can be executed in shared or separate computing devices or a combination thereof. For example, a plurality of the applications described herein can execute in the same computing device 103, or in multiple computing devices 103. Additionally, it is understood that terms such as "application," "service," "system," "engine," "module," and so on can be interchangeable and are not intended to be limiting.

Disjunctive language such as the phrase "at least one of X, Y, or Z," unless specifically stated otherwise, is otherwise understood with the context as used in general to present that an item, term, etc., can be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications can be made to the above-described embodiment(s) without departing substantially from the spirit and principles of the disclosure. All such modifications and variations are intended to be included herein within the scope of this disclosure and protected by the following claims.

Therefore, the following is claimed:

1. A system comprising one or more circuits, one or more processors, or any combination thereof, configured to at least:
generate a three-dimensional model of a patient from data received a three-dimensional imaging device in data communication with the one or more circuits, one or more processors, or any combination thereof;
identify a series of control points corresponding to movement of a three-dimensional model of a treatment machine; and
determine whether the three-dimensional model of the patient and the three-dimensional model of the treatment machine overlap at each one of the series of control points.

2. The system of claim 1, wherein the one or more circuits, one or more processors, or any combination thereof, are further configured to identify a collision between the patient and the treatment machine based at least in part on a determination that the three-dimensional model of the patient and the three-dimensional model of the treatment machine overlap at at least one of the series of control points.

3. The system of claim 1, wherein the data received from the three-dimensional imaging device is a point map provided by the three-dimensional imaging device.

4. The system of claim 1, wherein the one or more circuits, one or more processors, or any combination thereof, are further configured to at least:
interpolate an additional point based at least in part on at least two control points in the series of control points; and
determine whether the three-dimensional model of the patient and the three-dimensional model of the treatment machine overlap at the interpolated additional point.

5. The system of claim 1, wherein the series of control points is based at least in part on a trajectory of at least one of the patient or the treatment machine.

6. A system, comprising:
a data store comprising:
a three-dimensional model of a radiation treatment machine, and
a radiation treatment plan comprising a series of control points;
a computing device comprising a processor and a memory;
a three-dimensional imaging device in network communication with the computing device; and
machine readable instructions stored in the memory that, when executed by the processor, cause the computing device to at least:
generate a three-dimensional model of a patient based at least in part on data received from the three-dimensional imaging device;

align the three-dimensional model of the patient with a coordinate system of the three-dimensional model of the radiation treatment machine; and determine whether a collision between the three-dimensional model of the patient and the three-dimensional model of the radiation treatment machine will occur at each one of the series of control points of the radiation treatment plan.

7. The system of claim 6, wherein the data received from the three-dimensional imaging device comprises a point cloud.

8. The system of claim 6, wherein the machine readable instructions, when executed by the processor, further cause the computing device to at least:

interpolate a position between two control points in the series of control points; and determine whether a collision between the patient and the radiation treatment machine will occur at the interpolated position between the two control points.

9. The system of claim 6, wherein the radiation treatment plan is a first radiation treatment plan, the series of control points is a first series of control points, and the machine readable instructions, when executed by the processor, further cause the computing device to at least:

determine whether a collision between the patient and the radiation treatment machine will occur at each one of a second series of control points of a second radiation treatment plan in response to a determination that the collision between the patient and the radiation treatment machine will occur at at least one of the first series of control points of the first radiation treatment plan.

10. The system of claim 6, wherein the three-dimensional imaging device comprises a hand-held three-dimensional scanner.

11. A computer-implemented method, comprising:

generating, via a computing device, a three-dimensional model of a patient based at least in part on data received from a three-dimensional imaging device in network communication with the computing device;

aligning, via the computing device, the three-dimensional model of the patient with a coordinate system of a three-dimensional model of a radiation treatment machine; and determining, via the computing device, whether a collision between the patient and the radiation treatment machine will occur at each one of a series of control points of a radiation treatment plan.

12. The method of claim 11, further comprising approving, via the computing device, the radiation treatment plan in response to a determination by the computing device that the collision between the patient and the radiation treatment machine will not occur.

13. The method of claim 11, further comprising rejecting, via the computing device, the radiation treatment plan in response to a determination by the computing device that the collision between the patient and the radiation treatment machine will occur at at least one of the series of control points of the radiation treatment plan.

14. The method of claim 11, wherein the three-dimensional model of the patient comprises a mesh wire-frame and the data from the three-dimensional imaging device comprises a point cloud.

15. The method of claim 11, wherein determining whether a collision between the patient and the radiation treatment machine will occur comprises:

identifying, via the computing device, a bounded space occupied by the three-dimensional model of the patient at each one of the series of control points of the radiation treatment plan;

identifying, via the computing device, a bounded space occupied by the three-dimensional model of the radiation treatment machine; and determining, via the computing device, whether the bounded space occupied by the three-dimensional model of the patient overlaps, at least in part, the bounded space occupied by the three-dimensional model of the radiation treatment machine at each one of the series of control points of the radiation treatment plan.

* * * * *